United States Patent

Beach et al.

[11] 4,213,042
[45] Jul. 15, 1980

[54] CONTAINER CHIPPED CROWN RING DETECTOR

[75] Inventors: Donald J. Beach, Warson Woods; Robert J. Smith, Florissant, both of Mo.

[73] Assignee: Barry-Wehmiller Company, St. Louis, Mo.

[21] Appl. No.: 947,771

[22] Filed: Oct. 2, 1978

[51] Int. Cl.$^2$ .................................... G01N 21/32
[52] U.S. Cl. ........................... 250/223 B; 209/526; 356/240
[58] Field of Search ............... 250/223 B; 356/240; 209/526

[56] References Cited

U.S. PATENT DOCUMENTS

| | | |
|---|---|---|
| 3,267,796 | 8/1966 | Mathias . |
| 3,327,849 | 6/1967 | Sorbie . |
| 3,349,906 | 10/1967 | Calhoun . |
| 3,355,980 | 12/1967 | Mathias . |
| 3,479,514 | 11/1969 | Kidwell . |
| 3,631,255 | 12/1971 | Gender et al. . |

Primary Examiner—David C. Nelms
Assistant Examiner—Darwin R. Hostetter
Attorney, Agent, or Firm—Gravely, Lieder & Woodruff

[57] ABSTRACT

A container crown ring chip detector applying opto-electronic means for detecting the presence of chips in the container crown ring finish consisting of support means straddling the path of travel of the container crown ring, photo elements in opposing alignment and surrounding a substantial portion of the crown ring inspection station, electronic control means driving photo emitters which emit inspection rays detected by cooperating photo transistor receivers, and sequential driver circuits and synchronous detector circuits.

8 Claims, 5 Drawing Figures

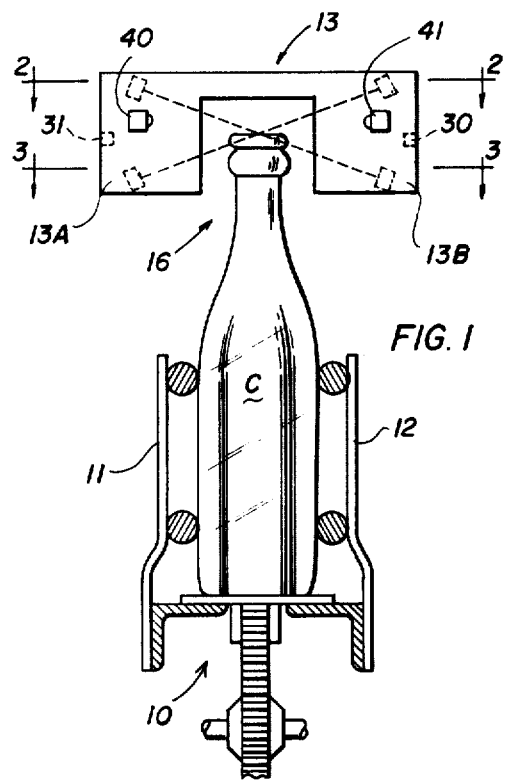
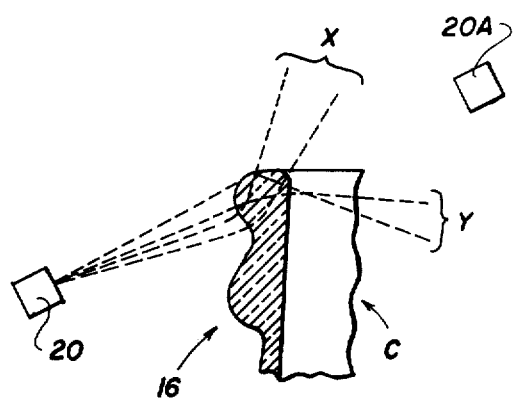
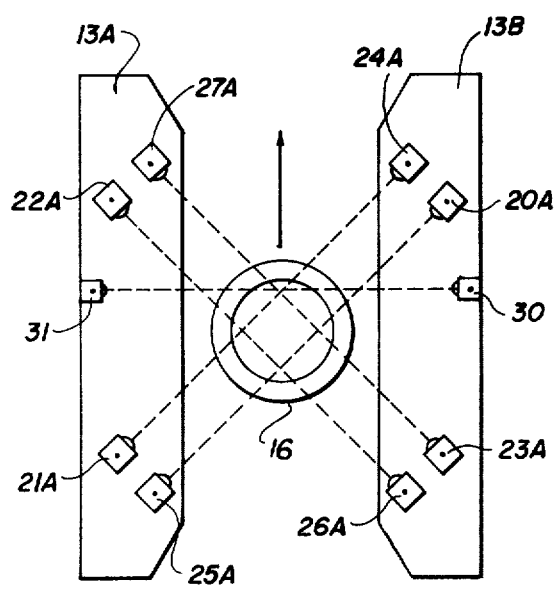
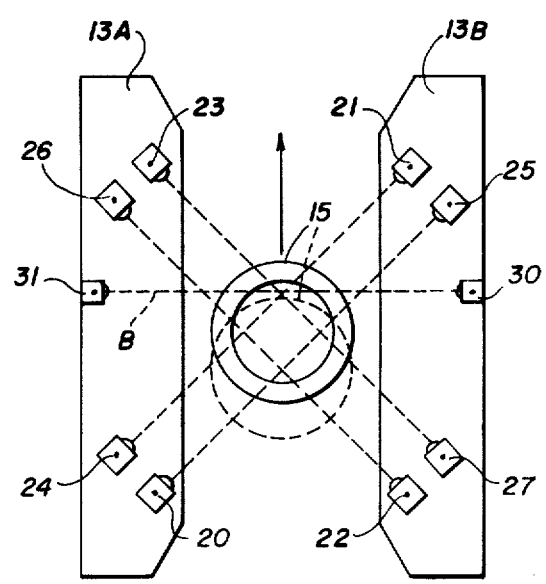
FIG. 1
FIG. 4
FIG. 2
RECEIVERS
FIG. 3
EMITTERS

CONTAINER CHIPPED CROWN RING DETECTOR

BACKGROUND OF THE INVENTION

The inspection of the crown ring of a container is important for a number of reasons, which include integrity of the crown ring to provide a proper seal, adequate surface area so the crown cap will seat properly, and avoidance of damage to the crown ring when the cap is removed.

Prior apparatus has included means for subjecting the crown ring to light beams on either the inside or outside and cooperating opposed detection means which is energized if a chip defect is present. Such apparatus has required rotating the inspection means or the container while interrupting the conveyance of the containers during the inspection period. Interrupting container movement is necessary when a part of the inspection apparatus must be inserted even partly into the container mouth.

Certain prior apparatus has effected container rim inspection by directing a beam of radiant energy of a polarized character so that the beam is given an electric vector perpendicular to the plane of incidence, and rotating the container to achieve the desired scan. Another type of inspection apparatus has relied upon illuminating the crown ring and looking at the illuminated crown ring through a rotating prism device, all without interfering with the high speed movement of the containers.

BRIEF DESCRIPTION OF THE INVENTION

This invention relates to improvements in container chipped crown detectors to allow for examination of the entire crown ring while the container is in motion.

The objects of the invention are to provide pairs of light emitting diodes and photo-transistor receivers for chip detectors, to provide a minimum number of pairs of the emitters and receivers to cover the complete crown ring finish area, to locate the emitters of light beams so that acceptable containers interrupt the beam sent out by the emitters, and to synchronize the paired emitters and receivers so that cross talk between adjacent inspection means will be eliminated.

In a preferred embodiment the present detector is organized to be insertable in a container conveyor line at a station where the crown ring inspection is associated with other means to inspect the bottom and other areas of a line of containers moving at the high speeds attained by current conveying equipment. More specifically a head structure is aligned to straddle the path of movement of containers being conveyed in single file so that a plurality of pairs of infrared light emitting diodes and photo transistor receivers can be located to carry out the scan of the entire crown ring for detecting chip defects.

The pairs of emitters and receiver-detectors are synchronously driven and monitored electronically so that the receiver is monitored only when its paired emitter is energized. Furthermore, non-adjacent pairs of emitters and receivers are energized in order to avoid and substantially eliminate cross talk effects on the receivers and false detection results. The complete scan of each container crown ring is accomplished in a scan cycle that takes about one millisecond. The short scan time eliminates timing errors at container speeds of up to 1200 containers per minute. The present detector can be provided with a container heighth detector so that too tall containers can be rejected.

The emitters are of the character which emit infrared beams, and these beams are required to pass through a chip defect in the container crown ring to cause a reject signal response. With containers that characteristically absorb infrared radiation, it is provided that the receivers can be set at a threshold sensitivity to a minimum infrared transmission level for detecting small chips, but there is then the possibility that containers with high infrared transmission characteristics will trigger a reject signal.

BRIEF DESCRIPTION OF THE DRAWINGS

The present invention may be illustrated by drawings wherein:

FIG. 1 is a fragmentary elevation of a flat to conveyor seen in section for conveying containers through an inspection station arranged with crown ring chip detector means;

FIG. 2 is an enlarged and fragmentary view taken along line 2—2 in FIG. 1 to illustrate an arrangement of light beam receiving means distributed around the container crown ring;

FIG. 3 is a view similar to FIG. 2 but taken along line 3—3 in FIG. 1 to show the arrangement of the light emitters paired with the receiving means of FIG. 2;

FIG. 4 is a diagram of the pattern of the light beam in relation to the lens action of the crown ring.

BRIEF DESCRIPTION OF THE INVENTION

Figure 5:
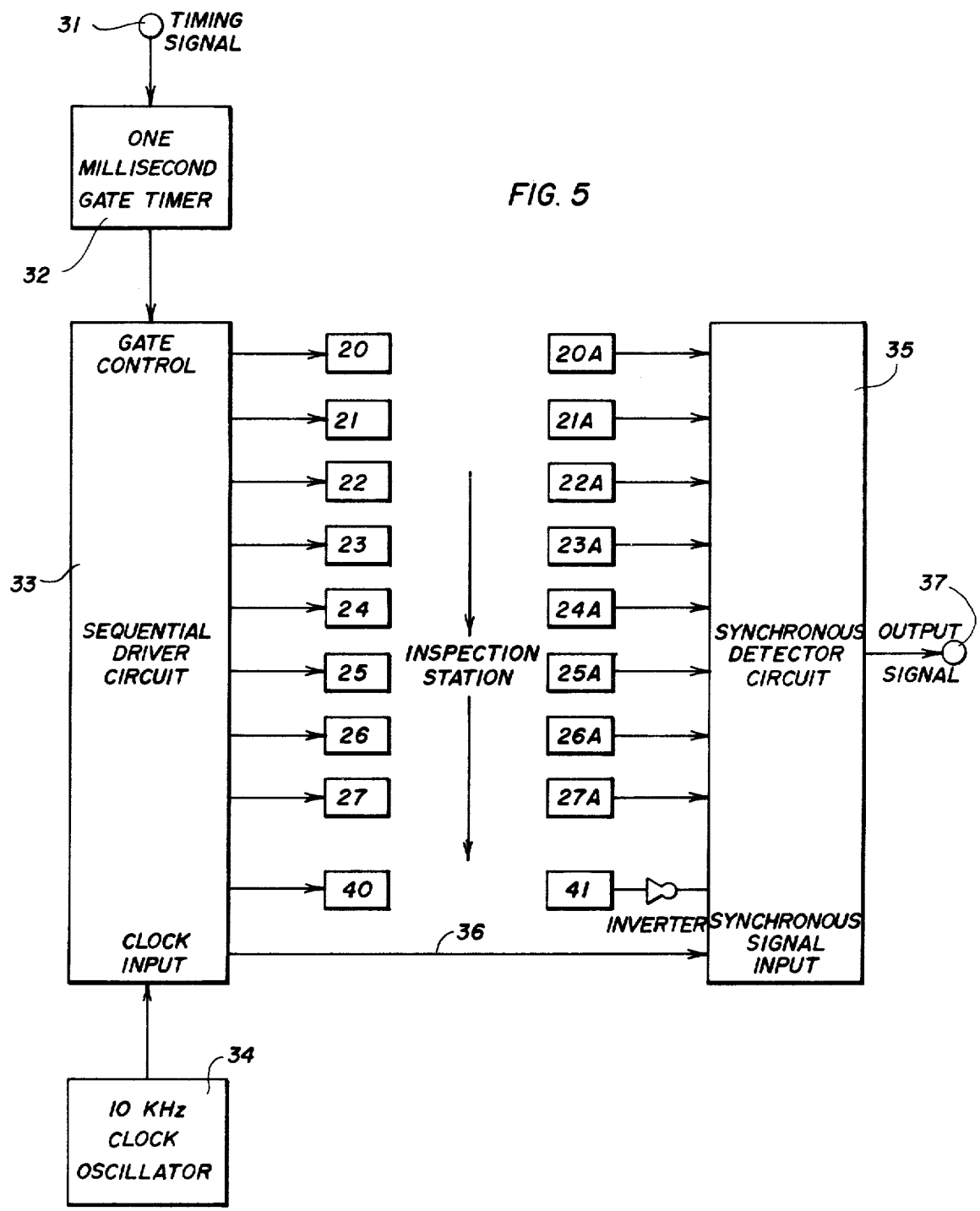
FIG. 5 is a block diagram of the electronic circuitry associated with the means seen in FIG. 1.

In FIG. 1 there is shown in somewhat abbreviated form a conveyor 10 and side guide fences 11 and 12 for keeping a line of containers C in a set path past a station where a crown ring chip detector device 13 is located by suitable support means (not shown) in position to straddle the crown rings as they pass through the station. The device 13 includes housings 13A and 13B in which are mounted the components to be described below. Any suitable conveyor apparatus may be employed, and at a suitable location beyond the inspection station a reject device (not shown) can be installed for removing containers found to be defective or unacceptable.

The internal means contained in housings 13A and 13B of the detector device 13 is seen in FIGS. 2 and 3. The installation herein preferred locates eight infrared light emitters 20 to 27 (FIG. 3) below the level of the crown ring portion 16 and the receivers above that portion 16 (FIG. 2). The receiver means 20A to 27A are shown in an arrangement where the leading edge 15 of the crown ring portion 16 is inspected first followed by the inspection of the trailing edge, and thereafter the areas between these edges are inspected. For the indicated direction of container movement in FIG. 3, the activation of the emitters is in the order of emitters 20, 21, 22,23 to catch the leading and trailing edges of the container. Then in order the activation follows for emitters 24, 25, 26 and 27. In the event that the crown ring is chipped a portion of the infrared light beam will pass beyond the crown ring and activate the receiver positioned in line with the projected beam. Each receiver is sensitive enough to generate a reject signal when the chip is of a size to permit approximately 50 percent of the infrared light beam to strike. Infrared emitting diodes and photo transistors are used because of their fast rise and fall times but visable light devices could be used with success at lower speeds.

The view of FIG. 4 is intended to illustrate an acceptable arrangement for the respective emitters, such as emitter 20 to be angled upwardly from the horizontal at approximately 12°. However, this angle may vary from about 10° to about 15°. The lens action of the crown ring on the container C is such that if there is no chip imperfection the infrared light beam will be scattered as shown by the arrows X and Y. On the other hand, if there is a chip imperfection in the crown ring some of the infrared light beam will pass beyond and be intercepted by the receiver 20A which is paired with the emitter 20. Test results have shown that a chip of approximately ⅛" in the crown ring can be detected almost every time. If the chip size gets smaller the detection achievement decreases until a chip size of ¼" can be detected approximately half the time. With containers that characteristically absorb infrared light, the detection threshold of the receivers may be set at a lower level so as to improve detection of small sized chips. At the lower levels, however, false rejections can be experienced when containers having high infrared transmission characteristics reach the inspection station. This feature is provided for by setting the receiver thresholds so they ignore a minimum transmission level.

The disposition of the emitters and the paired receivers, as seen in FIGS. 3 and 2 respectively, is such that the emitter beams impinge on the crown ring area at eight substantially equally spaced target sectors. The beams have a spread angle of about 10° so that with eight beams the entire crown ring can be irradiated with infrared light. As shown in FIG. 4, the vertical displacement of the receiver 20A is at substantially the same angle as its paired emitter 20 so as to be in the line of aim of the emitter.

In order to trigger the detector 13 into action, each time a container enters the inspection station the leading edge 15 of the crown ring 16 breaks a light beam B which is established between a light source 30 and a photocell 31. The photocell 31 transmits a signal to a timing start device 32. The duration of the time period may be as short as one millisecond so that a complete scan of the crown ring of each container C can be obtained.

FIG. 5 illustrates the electronic means for effecting the sequential activation of the emitters. The signal from the photocell 31 indicates that a container C is in position for crown ring inspection. That signal triggers a one millisecond timer 32 which applies a one millisecond "ON" signal to the sequential driver circuit 33 and allows that driver to operate for that period of time. The receivers 20A through 27A are in a synchronous detector circuit 35 so that if an emitter beam passes a crown ring chip its receiver will be activated in synchronism through a circuit connection 36. The driver 33 is clocked through its sequence by a 10 kilo-hertz clock oscillator 34 which sequentially energizes the eight infrared emitters (LED's) 20 to 27 for one-tenth of one millisecond each. After the final emitter 27 is energized, the driver circuit is stopped and requires a new signal from the photocell 31 to go through its sequential cycle. It is shown in FIGS. 2, 3 and 5 that no adjacent emitters are energized in sequence. The adjacent receiver to an operating emitter beam pair receives about fifty percent cross talk radiation. The synchronous detector circuit 35 ignores the cross talk signal, but if the last inspection were to be started with the partially energized receiver, the additional directed infrared radiation beam from its associated emitter might cause an abnormally high output which would be intercepted in the detector circuit 35 as a reject signal. The receiver transistors utilized in the synchronous detector circuits 35 have specific rise and fall times for their outputs and can falsely be altered by pre-radiation from beams directed to adjacent receivers. By arranging the sequence of activity of the emitters so that no two adjacent emitters are activated in sequence, pre-radiation can be avoided.

The inspection order is important, not only for the avoidance of cross talk radiation, but to initiate inspection of the leading and trailing edges of the crown ring at the beginning of each inspection cycle. This is important because the containers are moving during inspection so that a trailing emitter could miss the crown ring if inspected last and the leading emitter would be too far off target.

As shown in FIG. 1 the detector device 13 is provided with a special emitter 40 and a receiver 41 for the purpose of detecting containers that are too tall. The light beam from the emitter 40 would be intercepted by a too tall container so as to break the beam directed at its receiver 41, and this would initiate a signal through an inverter 42 connected in series to the detector circuit. The inverter reverses the logic so that when the receiver 41 has no output at the time of inspection the detector circuit generates an output for reject purposes. The emitter 40 is connected into the sequential driver circuit 33 in a manner that prevents loss of synchronization. The synchronous detector circuit 35 operates to inspect the output level of the matching receiver transistors associated with the emitters, and if a particular receiver has an output at the moment its emitter is energized, the detector circuit 35 delivers an output signal 37 which is used to trigger the container reject system. It is important that a receiver is monitored only when its associated emitter is energized so as to avoid cross talk or false detection.

The foregoing disclosure of a container chipped crown ring detector may be modified in certain particulars without departing from the method of inspecting containers for crown ring defects.

What is claimed is:

1. Container crown ring defect detector means comprising: means for moving containers in single file through an inspection station with the crown rings moving in a common path; defect detection means adjacent the common path of the crown rings in the inspection station, said defect detection means incorporating a plurality of pairs of elements in which there is a light emitter and a light receiver in each pair in beam path alignment through the container crown rings moved through the inspection station; circuit means connected to said plurality of pairs of elements for energizing said light emitters in a predetermined order and for simultaneously monitoring said receivers in the order of energization of said light emitters; and means connected with said receivers for rejecting a container associated with the activation of a receiver by light from its paired light emitter.

2. The detector means set forth in claim 1, wherein said light emitters project infrared light beams with a spread angle of about 10°.

3. The detector means set forth in claim 1, wherein there are at least eight pairs of elements spaced in the inspection station and arranged to cover eight substantially equally spaced areas on the crown ring of the container.

4. The detector means set forth in claim 1, wherein said light emitters and receivers are spaced from the path of the crown ring substantially the same distances for developing substantially equal levels of light intensity and activation from received light.

5. The detector means set forth in claim 1, wherein said light emitters are disposed below and said light receivers are disposed above the crown ring position in the inspection station.

6. The detector means set forth in claim 1, wherein said circuit means includes a sequential driver circuit connected to said light emitters, a synchronous detector circuit connected to said light receivers, means operated by the arrival of a container at said inspection station to apply a start signal to said driver circuit, clock means connected into said driver circuit for causing said sequencing of said light emitters, and circuit connection means between said clock means and said detector circuit for synchronizing said light receivers with said light emitters in said pairs.

7. The detector means set forth in claim 6, wherein said container operated means applies a start signal of substantially one millisecond, and said clock means causes said driver circuit to sequentially energize said light emitters each for substantially one-tenth of one millisecond.

8. The detector means set forth in claim 6, wherein said driver circuit sequences said light emitters in a pattern for preventing cross talk energization of non-paired light receivers.

* * * * *